US008109963B1

(12) United States Patent
Korrol

(10) Patent No.: US 8,109,963 B1
(45) Date of Patent: Feb. 7, 2012

(54) METHOD AND APPARATUS FOR RELIEVING MENSTRUAL DISCOMFORT

(76) Inventor: Jay Korrol, West Palm Beach, FL (US)

( * ) Notice: Subject to any disclaimer, the term of this patent is extended or adjusted under 35 U.S.C. 154(b) by 0 days.

(21) Appl. No.: 12/757,952

(22) Filed: Apr. 9, 2010

Related U.S. Application Data

(63) Continuation-in-part of application No. 11/243,927, filed on Oct. 5, 2005, now abandoned.

(51) Int. Cl.
*A61B 17/00* (2006.01)
(52) U.S. Cl. ........................................ 606/204
(58) Field of Classification Search .................. 606/201, 606/203, 204
See application file for complete search history.

(56) References Cited

U.S. PATENT DOCUMENTS

| | | | | |
|---|---|---|---|---|
| 4,479,495 | A * | 10/1984 | Isaacson | 606/204 |
| 4,716,898 | A * | 1/1988 | Chauve et al. | 606/204 |
| 5,078,728 | A * | 1/1992 | Giarratano | 606/204 |
| 5,295,996 | A | 3/1994 | Blair | |
| 5,701,608 | A | 12/1997 | Kohn | |
| 5,792,176 | A | 8/1998 | Chang | |
| 6,152,140 | A * | 11/2000 | Blum | 128/898 |
| 6,282,443 | B1 | 8/2001 | Mann et al. | |
| 6,711,750 | B1 | 3/2004 | Yoo | |

* cited by examiner

*Primary Examiner* — Elizabeth Houston
*Assistant Examiner* — Julie A Szpira
(74) *Attorney, Agent, or Firm* — Gold & Rizvi, P.A.; Glenn E. Gold; H. John Rizvi

(57) ABSTRACT

An pressure applicating band kit for treatment of menstrual cramps includes a flexible strap with a buckle and a free end. A stylus is attached to the buckle for applying pressure to a menstrual discomfort controlling pressure point on the patient's body when the strap is fastened. Cooperating fasteners are on the free end of the strap and the strap for securing the strap and maintaining pressure on the controlling pressure point. Software is also in the kit, which directs the operation of the treatment. The menstrual discomfort controlling pressure point is identified by applying light pressure to a menstrual discomfort controlling pressure region. The points that are most tender are considered the menstrual discomfort controlling pressure points. The pressure applicating band can comprise one or more stylus for applying pressure to one or more points to optimize the relief process.

19 Claims, 6 Drawing Sheets

METHOD AND APPARATUS FOR RELIEVING MENSTRUAL DISCOMFORT

CROSS-REFERENCE TO RELATED APPLICATION

This Continuation-In-Part Application claims the benefit of co-pending U.S. Non-Provisional patent application Ser. No. 11/243,927, filed on Oct. 5, 2005, which is incorporated herein in its entirety.

FIELD OF THE INVENTION

This invention relates to the field of menstrual discomfort management by application of pressure to a respective pain management region of one's body.

BACKGROUND OF THE INVENTION

Acupuncture has long been an accepted method of treatment in Oriental medicine guided by the principles that the body has meridians in which Qi (energy) flows. Each meridian represents a different organ and each organ represents different aspects and functions. Each meridian has its own set of points and these points also represent different aspects and functions within that meridian's organ. There are certain points in all meridians that have specific functions in common.

By inserting needles at various points in the body along the meridians, the flow of internal energy is redirected bringing relief to the sufferers of various maladies. There are many texts on the subject which teach the location of acupuncture points in the body along with which point is beneficial for treatment of certain symptoms. By inserting the needles at specific points, a particular malady or its symptoms can be successfully treated. There has been a lack of general acceptance of acupuncture resulting from skepticism regarding the theory and reluctance to undergo the needle punctures with the attendant possibility of localized pain and infection.

It has now been determined that acupressure which teaches merely applying external pressure to the acupuncture points on the body can have the same or similar results without the need of needle punctures. Such treatment clearly overcomes a patient's fear of needle sticks and infection.

The skilled practitioner of acupuncture/acupressure is trained in the diagnosis required by this 2000 year old art and the selection of the treatment site on the patient's body that will produce beneficial effects for the diagnosed malady. There are a great many acupoints on the body, the location of each usually described in anatomical terms. The art in the practice is the selection of the proper acupoint or acupoints to use when a malady involves more than one organ and meridian. The skilled artisan can precisely locate these points to bring the full effect of the treatment to bear accurately and squarely on the selected point. The patient's relief may be immediate. In syndromes with recurring cycles, such as problems associated with menstruation, repeated acupressure treatment may be required at the onset of each episode of symptoms.

One of the sets of points in all meridians is known as, "Accumulation Points." Each meridian has one. The main function of these points is for, "acute," (sudden onset) patterns accompanied by pain. The particular point of interest here is the accumulation point along the Spleen meridian, specifically the 8th (Sp 8) of the 21 points that belong to the Spleen meridian.

There have been attempts to bring the benefits of acupressure to the public through self-help publications and apparatus to be applied to various parts of the body.

DESCRIPTION OF THE PRIOR ART

U.S. Pat. No. 6,282,443 issued Aug. 28, 2001 to Mann et al teaches a wrist band which applies an electric current to the body to treat menstrual cramps.

U.S. Pat. No. 5,701,608 issued Dec. 30, 1997 to Kohn teaches an undergarment brief with a pressure insert mounted on an elastic panel for applying pressure to the abdominal area to relieve menstrual cramps.

U.S. Pat. No. 4,479,495 issued Oct. 30, 1984 to Isaacson teaches an elastic band with dense hook and loop fasteners carrying a flexible protuberance to be applied about different parts of the body, as the consumer sees fit, so that the protuberance contacts an acupoint. To use the device, the consumer would have to be skilled in the Chinese diagnoses of a malady, make the correct diagnoses, and correctly select one acupoint to treat the diagnosed malady.

U.S. Pat. No. 6,711,750 issued Mar. 30, 2004 to Yoo teaches the use of an elastic belt with adjustable acupressure pads, in addition to heat pads, for placement about the waist of a user. The belt may have dense hook and loop fasteners for connecting the ends together.

U.S. Pat. No. 5,792,176 issued Aug. 11, 1998 to Chang teaches the use of an adhesive pad supporting a rigid nub for applying pressure to a selected point on the body.

What the prior art lacks is a teaching of a specific apparatus to be applied to a specific location to treat a specific malady accompanied with the clear instructions of how and where the consumer is to apply the apparatus.

SUMMARY OF THE INVENTION

Accordingly, it is a primary objective of the instant invention to teach the construction of a pressure applicating band carrying a stylus or plurality of stylus's for applying pressure to a menstrual discomfort controlling pressure point on a body of a patient.

It is a further objective of the instant invention to teach the use of a kit containing an pressure applicating band with detailed instructions informing the consumer to correctly place and apply the band.

It is yet another objective of the instant invention to teach the construction of a pressure applicating band wherein the stylus is located for maximum sustained pressure.

It is another objective to teach a method of locating a menstrual discomfort controlling pressure point. The subject identifies a tender location on the inner, rear calf on ether leg and continuously applies a pressure until the discomfort diminishes.

It is yet another objective to utilize a plurality of pressure stylus's to apply a pressure about a region proximate the menstrual discomfort controlling pressure point.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE DRAWINGS

The invention will now be described, by way of example, with reference to the accompanying drawings, where like numerals denote like elements and in which.

Like reference numerals refer to like parts throughout the various views of the drawings.

DETAILED DESCRIPTION OF THE INVENTION

Figure 1:
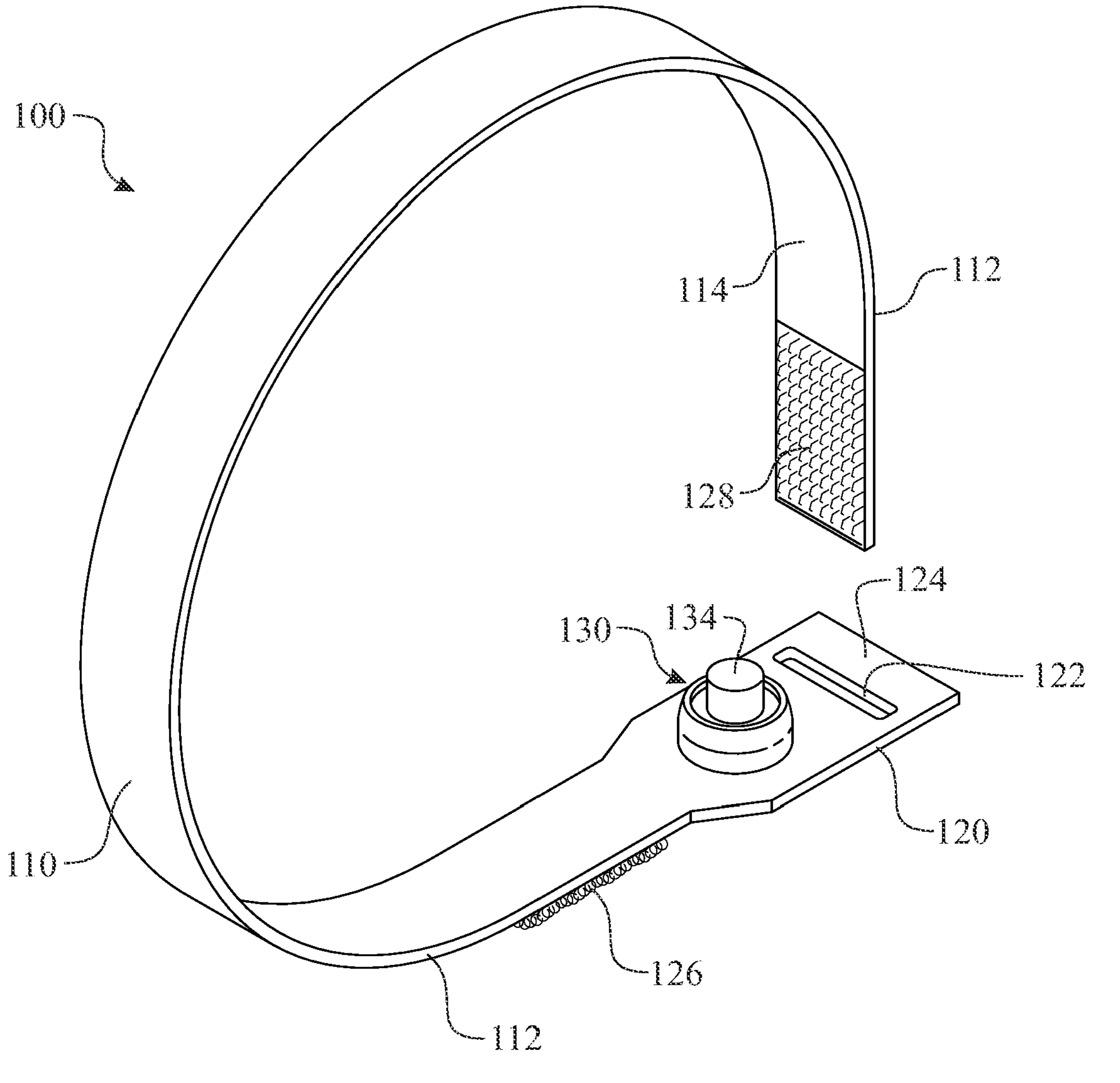
FIG. 1 is a perspective view of an exemplary pressure applicating band.

The following detailed description is merely exemplary in nature and is not intended to limit the described embodiments or the application and uses of the described embodiments. As used herein, the word “exemplary” or “illustrative” means “serving as an example, instance, or illustration.” Any implementation described herein as “exemplary” or “illustrative” is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms “upper”, “lower”, “left”, “rear”, “right”, “front”, “vertical”, “horizontal”, and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The pressure applicating band 100, shown in FIGS. 1-4, has a flexible band strap 110, a buckle 120 and a pressure applicating stylus 130. The buckle 120 has a buckle aperture 122 through which the strap free end 116 of the band passes to engage the first dense hook and loop interface portion 126 on the strap outer surface 112 of the flexible band strap 110. The strap inner surface 114 of the strap free end 116 has a cooperating patch of dense hook and loop interface portion 128 attached thereto. The dense hook and loop interface is commonly referred to by the trade name VELCRO. One dense hook and loop interface portion 126, 128 comprising a series of small loops formed on a mating surface. The cooperating dense hook and loop interface portion 128, 126 comprising a series of upstanding hooks formed on a respective mating surface. When the two surfaces are pressed together, the hooks and loops engage to form a releasable connection.

The flexible band strap 110 may be formed of a solid plastic ribbon which is flexible enough to be coiled on itself but not necessarily resilient to prevent stretching when the band is placed on the patient’s body under tension. Other materials may be used, such as textiles or metal or plastic meshes, to form a band with the requisite properties.

The buckle 120 may be formed as a unitary extension of the flexible band strap 110 or as a separate component permanently affixed to the band. The pressure applicating stylus 130 is molded or otherwise formed on the inside surface of the buckle. Alternatively, the stylus base 132 of the stylus may be adhered to the surface of the buckle by autologous bonding using heat and pressure or the use of compatible adhesives.

Figure 2:
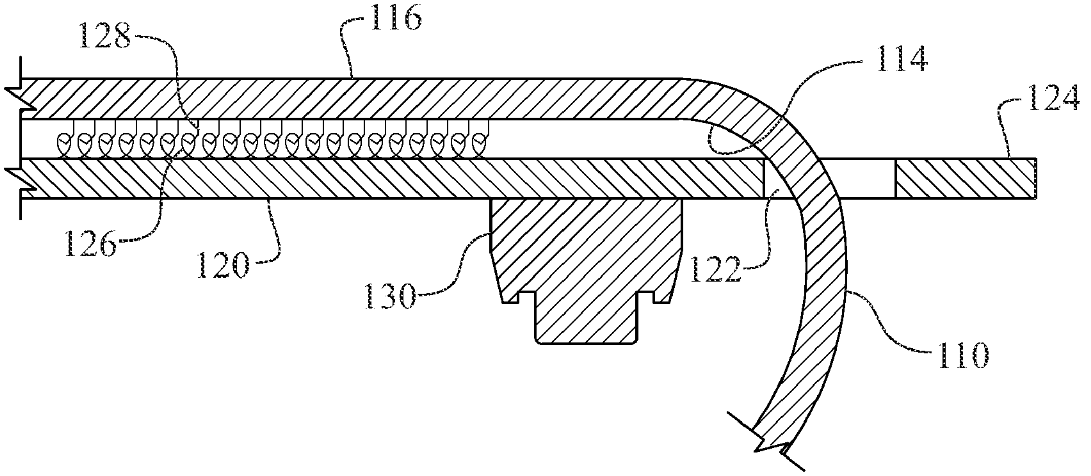
FIG. 2 is a cross sectional view of the pressure applicating band and buckle of this invention.

The free end of the buckle is formed as a buckle tab 124 to facilitate the user grasping the buckle in one hand. The strap free end 116 of the band is inserted through the buckle aperture 122 in the buckle and the user grasps the end of the band with the other hand. By moving the hands apart, the circumference of the band is reduced applying pressure to the encircled body part of the patient and applying tension to the band. By locating the stylus immediately adjacent the overlap of the ends of the belt, the amount of compression is greatest and can be accurately controlled by adjusting the band length. When the desired amount of pressure is generated by the band, the dense hook and loop swatch on the free end of the band is brought into contact with the dense hook and loop swatch on the outside surface of the band to fix the band in place, as shown in FIG. 2. Of course, other releasable fasteners may be mounted on the band.

Figure 3:
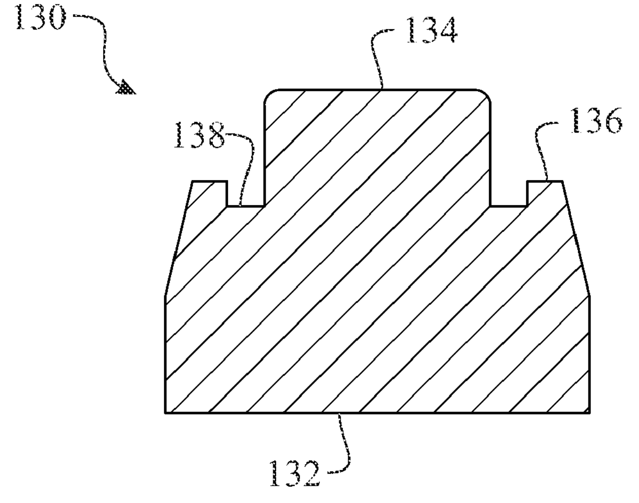
FIG. 3 is a cross sectional of an exemplary stylus.
Figure 4:
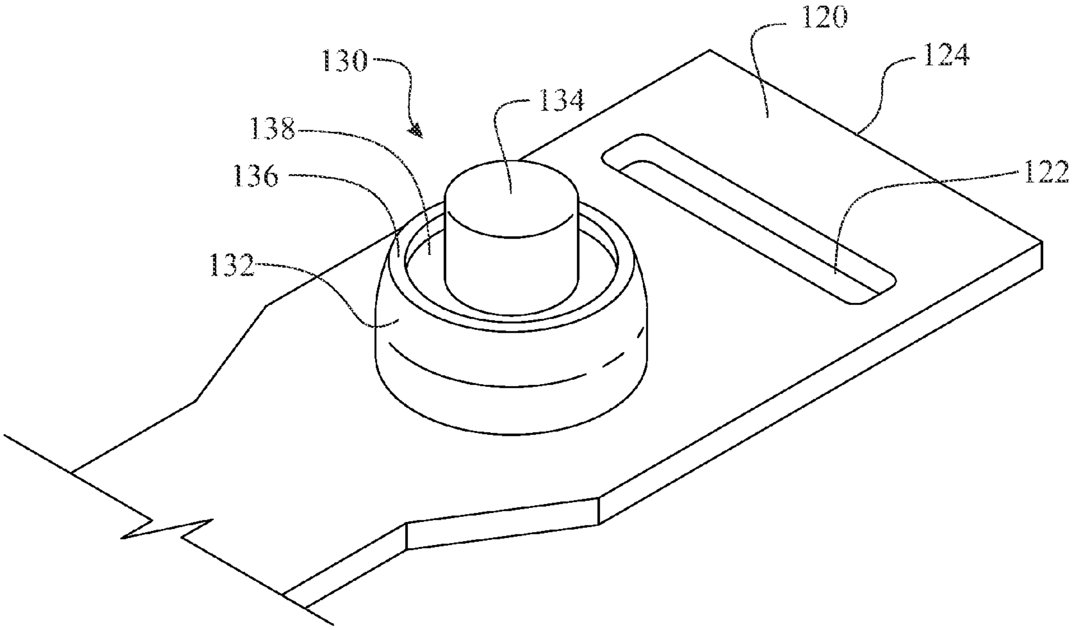
FIG. 4 is a top isometric view of the stylus and buckle of this invention.

The pressure applicating stylus 130, shown in FIGS. 3 and 4, may be formed of plastic, carbon fibers, metal, ceramic, wood, bone or other suitable material compatible with skin contact. The stylus is designed to apply pressure to a point on the patient’s body that produces the equivalent result of acupuncture. The stylus base 132 is permanently connected to the buckle 120 and is of sufficient diameter to stabilise the stylus perpendicular to the buckle. The stylus tapers from said base toward a smaller distal end. The stylus has a stylus peripheral relief ring 138 with a surrounding stylus peripheral relief ridge 136 near the distal end. The distal end of the stylus extends from the inner surface of the relieved ring beyond the stylus peripheral relief ridge 136 and terminates in a small, stylus pressure applicating surface 134. The end should be of such a size that it will not penetrate the skin when the band is tightened to the optimum pressure but will transmit a concentrated force on the acupressure point. The stylus peripheral relief ring 138 and stylus peripheral relief ridge 136 serve to tighten the patient’s skin around the stylus and flatten the underlying tissue to concentrate the pressure on the acupressure point. The skin and underlying tissue partially fills the relieved ring to provide resistance to movement of the stylus either by muscular movement of the patient or external forces. It is understood that the pressure applicating stylus 130 can be of any reasonable form factor for applying a pressure to the desired area.

Figure 5:
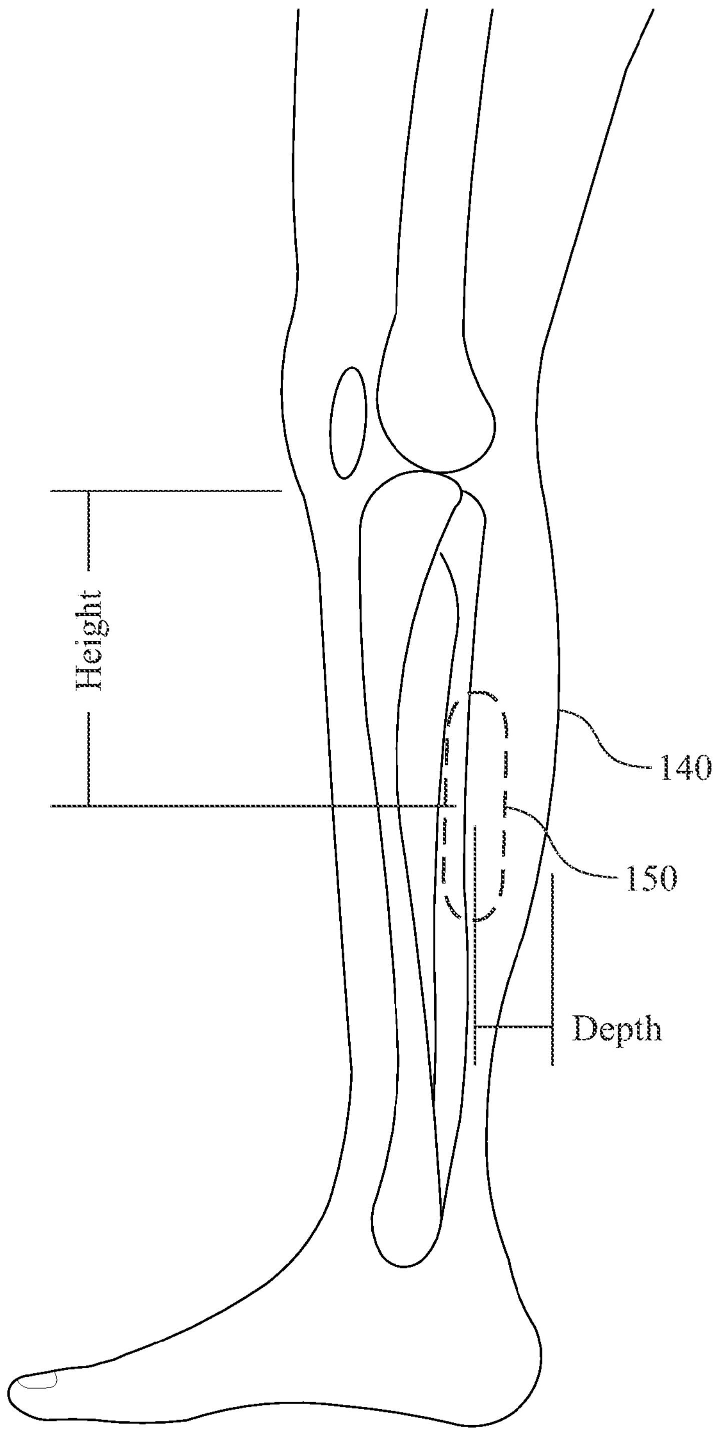
FIG. 5 is a side elevation view being a representation of a general region for locating a menstrual discomfort controlling pressure point.
Figure 6:
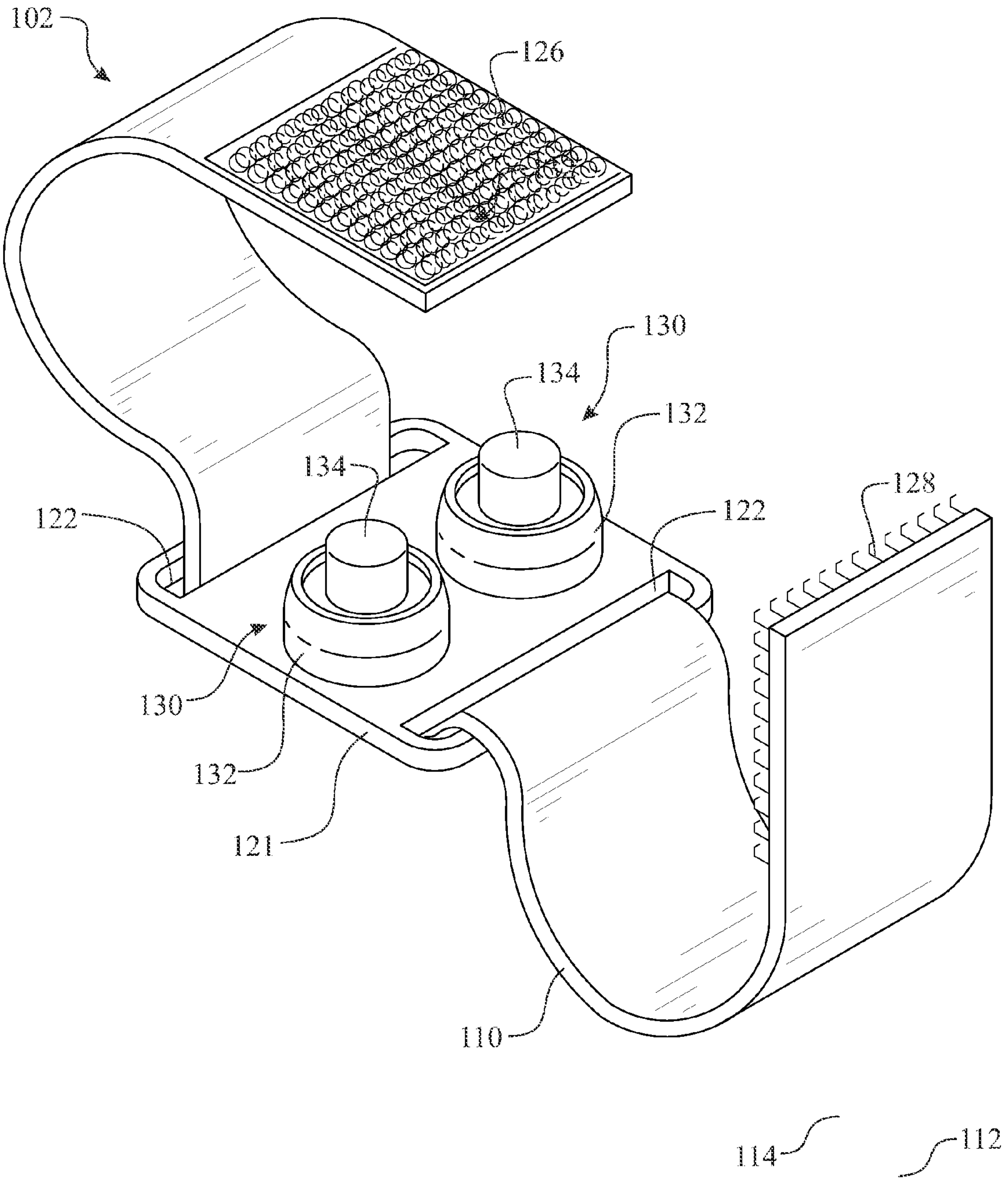
FIG. 6 is an isometric view of an alternate exemplary pressure applicating band.

Although one means of applying pressure is by identifying a specific acupressure point, it was recognized by the inventor while continuing development of the product and process, that the acupressure point is not accurate. Although the acupressure point can provide some aid, it was identified that improved results were achieved by identifying a specific menstrual discomfort controlling pressure point. The menstrual discomfort controlling pressure point is located within a region on the calf 140 referred to as a menstrual discomfort controlling pressure region 150 as illustrated in FIG. 5. The menstrual discomfort controlling pressure region 150 is generally located on the inner calf at a height of 3-4" below the lower edge of the knee cap and 1-2" from the rear edge of the calf towards the inner calf region. It has been identified that there are normally 2-3 tender spots in the menstrual discomfort controlling pressure region 150. A plurality of pressure applicating stylus 130 is disposed upon a pressure supporting plate 121 as shown on a multi-pressure applicating band 102 illustrated in FIG. 6. The plurality of pressure applicating stylus 130 distributes the pressure across a plurality of menstrual discomfort controlling pressure points to optimize the process.

Figure 7:
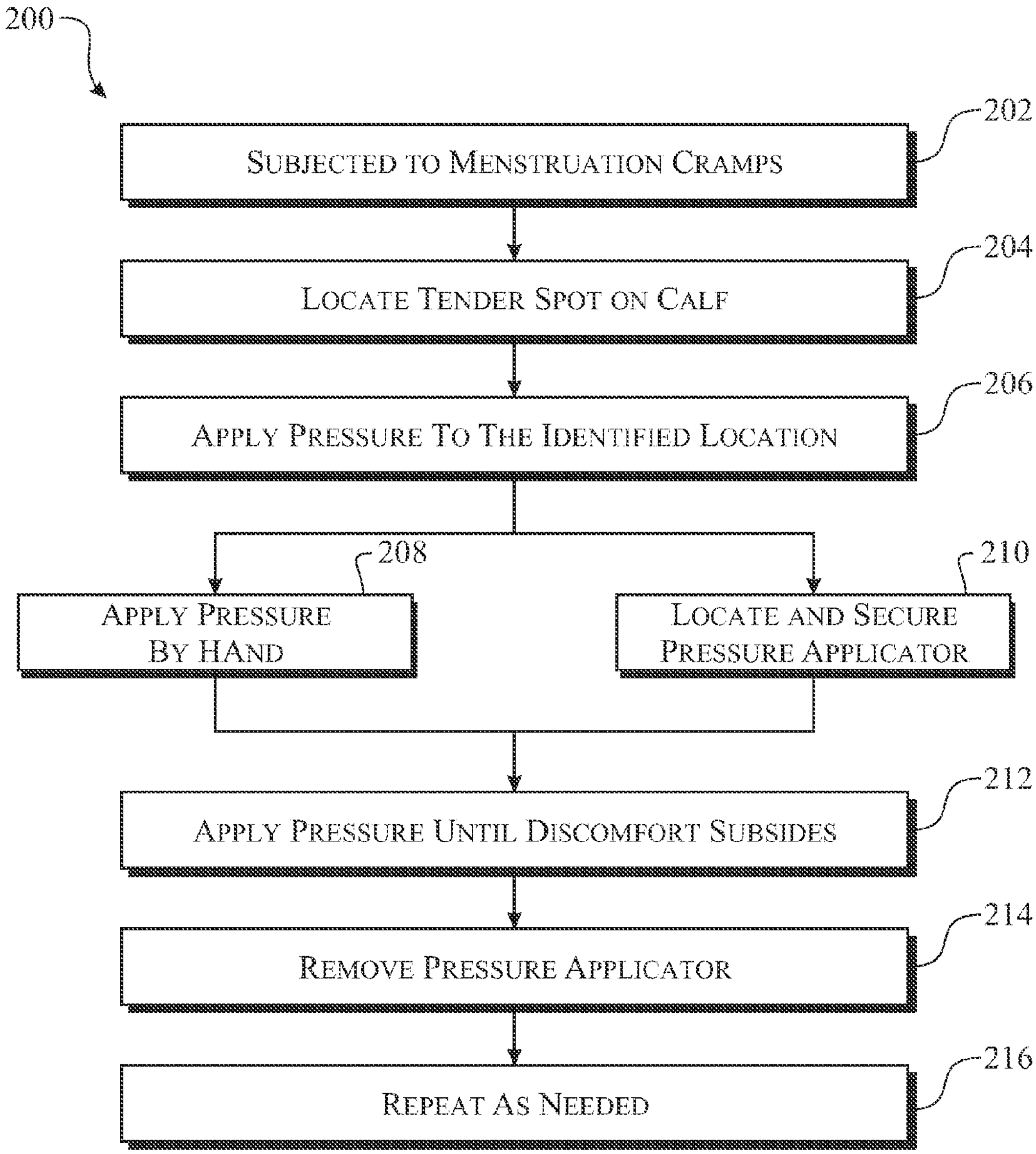
FIG. 7 is an exemplary flow diagram in accordance with the present invention.

A method of relieving discomfort resulting from menstruation is illustrated in a series of steps of a menstrual discomfort relief flow method 200 presented in FIG. 7. The menstrual discomfort relief flow method 200 is initiated when a person recognizes they are being subjected to discomfort resulting from menstruation 202. The person feels about the menstrual discomfort controlling pressure region 150 to locate the tender spot 204 within the menstrual discomfort controlling pressure region 150 on either calf 140. The person then applies a pressure to the tender area 206. The pressure can be applied by hand 208 or using a pressure applicating band 100, 102. The user would secure the pressure applicating band 100, 102 aligning the stylus pressure applicating surface 134 with the identified tender spots, in accordance with a locate and secure a pressure applicator step 210. The pressure is applied until the discomfort subsides 212. This is normally accomplished within 5 minutes. Once the discomfort subsides, the user can remove the application 214. If the discomfort continues, the user can remove the application 214 and repeat the step of locating the tender spot 204 to ensure the applicator is properly positioned. If the discomfort returns, the user can repeat 216 the menstrual discomfort relief flow method 200.

It is recognized that the pressure applicating stylus 130 can be disposed upon the flexible band strap 110 or simply positioned against the strap inner surface 114 and secured by the applied pressure.

The pressure applicating band is supplied with software necessary to the proper use of the device. The software may be in the form of a printed brochure, an audio tape, a floppy disk, or video disk (DVD) accompanying the band and forming a kit. The patient is instructed in the theory of acupressure, the anatomical location of the particular acupoint that relates to the malady to be treated is shown in illustrations or video, as well as, the correct amount of force to be used and the time frame of treatment.

Example

Menstrual cramps are a recurring painful malady associated with the menstrual cycle. The pressure applicating band of this invention can provide relief from this malady. One means for obtaining relief of the discomfort is to apply pressure to an acupressure point, more specifically, SP 8. As shown in the software, the location of SP 8 is approximately 3 cun (inches) below the lower border of the medial condyle of the tibia and approximately 1 inch from the edge of the tibia. The measurements are approximate because the locations will be different for different sized women.

As shown by the software, the proper method of determining the location of SP 8, the acupoint, is by the patient's own proportions. 3 cun is the distance between the index finger and the little finger on each hand. To identify SP 8, the patient uses their own hand. Place the right hand on the inside of the left calf with the right index finger at the lower border of the medial condyle of the tibia. The little finger rests on the approximate position of SP 8. Apply the stylus to this spot and fix the band around the leg. Tighten the band to a level that is tolerable, without causing pain, and secure the fasteners. The cramps should begin to diminish and disappear.

More recently, it has been found that the acupressure point SP 8 will produce reasonable results, wherein locating a precise menstrual discomfort controlling pressure point. The menstrual discomfort controlling pressure point can differ from the acupressure point SP 8. The acupressure point SP 8 can be one or more specific points, identified by touch. The user would apply light pressure about the menstrual discomfort controlling pressure region 150 to identify one or more tender locations. The tender locations are the menstrual discomfort controlling pressure points. The user then applies pressure to each of these points. This process of identifying the menstrual discomfort controlling pressure points, optimizes the relief process. The use of a plurality of pressure applicating stylus 130 additionally enhances the relief process.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What I claim is:

1. A method of relieving discomfort resulting from menstruation comprising the steps of:
- palpitating a calf region until locating a tender spot, wherein the calf region is defined as an area on an inner calf at a height of 3 to 4 inches below a lower edge of the knee cap and 1 to 2 inches from a rear edge of the calf towards the inner calf;
- defining said tender spot as a temporary menstrual discomfort controlling pressure point, wherein said tender spot varies in location within the calf region over time; and
- applying a pressure to the menstrual discomfort controlling pressure point for a period of time until the discomfort is reduced.

2. A method of relieving discomfort resulting from menstruation as recited in claim 1, the method further comprising a step of securing a pressure applicating band comprising a band strap and a stylus, wherein the stylus is positioned in registration with the menstrual discomfort controlling pressure point.

3. A method of relieving discomfort resulting from menstruation as recited in claim 2, the method further comprising a step of concentrating the applied pressure wherein the stylus is tapered from a base towards a contacting end which is smaller than the base.

4. A method of relieving discomfort resulting from menstruation as recited in claim 2, the method further comprising a step of securing the pressure applicating band in located by wrapping the band about the persons' leg securing the band in location utilizing a dense hook and tape loop interface.

5. A method of relieving discomfort resulting from menstruation as recited in claim 2, the method further comprising a step of assembling the stylus to the pressure applicating band via a pressure supporting plate, the band being assembled to the pressure supporting plate by inserting the band through at least one aperture within the pressure supporting plate.

6. A method of relieving discomfort resulting from menstruation as recited in claim 1, the method further comprising a step of securing a pressure applicating band comprising a band strap and a plurality of stylus, wherein at least one of the plurality of stylus is positioned in registration with the menstrual discomfort controlling pressure point.

7. A method of relieving discomfort resulting from menstruation as recited in claim 6, the method further comprising a step of securing the plurality of stylus in position using a pressure supporting plate, wherein the plurality of stylus are disposed upon the pressure supporting plate, the band being assembled to the pressure supporting plate by inserting the band through at least one aperture through the pressure supporting plate.

8. A method of relieving discomfort resulting from menstruation comprising the steps of:

palpitating a calf region until locating a tender spot, wherein the calf region is defined as an area on an inner calf at a height of 3 to 4 inches below a lower edge of the knee cap and 1 to 2 inches from a rear edge of the calf towards the inner calf;

defining said tender spot as a temporary menstrual discomfort controlling pressure point, wherein said tender spot varies in location within the calf region over time; and applying a pressure to the menstrual discomfort controlling pressure point for a period of time until the discomfort is reduced utilizing a pressure applicating band comprising a band strap and a stylus;

positioning the stylus in registration with the menstrual discomfort controlling pressure point; and securing the band strap about one's calf via a securing connector attached to at least one end of the band strap.

9. A method of relieving discomfort resulting from menstruation as recited in claim 8, the method further comprising a step of concentrating the applied pressure wherein the stylus is tapered from a base towards a contacting end which is smaller than the base.

10. A method of relieving discomfort resulting from menstruation as recited in claim 8, the method further comprising a step of adjustably securing the band using wherein utilizes a dense hook and tape loop interface as the securing connector.

11. A method of relieving discomfort resulting from menstruation as recited in claim 8, the method further comprising a step of assembling the stylus to the pressure applicating band via a pressure supporting plate, the band being assembled to the pressure supporting plate by inserting the band through at least one aperture within the pressure supporting plate.

12. A method of relieving discomfort resulting from menstruation as recited in claim 8, the method further comprising a step of securing a pressure applicating band comprising a band strap and a plurality of stylus, wherein at least one of the plurality of stylus is positioned in registration with the menstrual discomfort controlling pressure point.

13. A method of relieving discomfort resulting from menstruation as recited in claim 12, the method further comprising a step of securing the plurality of stylus in position using a pressure supporting plate, wherein the plurality of stylus are disposed upon the pressure supporting plate, the band being assembled to the pressure supporting plate by inserting the band through at least one aperture through the pressure supporting plate.

14. A method of relieving discomfort resulting from menstruation comprising the steps of:

palpitating a calf region until locating a tender spot, wherein the calf region is defined as an area on an inner calf at a height of 3 to 4 inches below a lower edge of the knee cap and 1 to 2 inches from a rear edge of the calf towards the inner calf;

defining said tender spot as a temporary menstrual discomfort controlling pressure point, wherein said tender spot varies in location within the calf region over time; and applying a pressure to the menstrual discomfort controlling pressure point for a period of time until the discomfort is reduced utilizing a pressure applicating band comprising a band strap and a stylus, the stylus being disposed upon to the band strap;

positioning the stylus in registration with the menstrual discomfort controlling pressure point; and securing the band strap about one's calf via a securing connector attached to at least one end of the band strap.

15. A method of relieving discomfort resulting from menstruation as recited in claim 14, the method further comprising a step of concentrating the applied pressure wherein the stylus is tapered from a base towards a contacting end which is smaller than the base.

16. A method of relieving discomfort resulting from menstruation as recited in claim 14, the method further comprising a step of adjustably securing the band using wherein utilizes a dense hook and tape loop interface as the securing connector.

17. A method of relieving discomfort resulting from menstruation as recited in claim 14, the method further comprising a step of assembling the stylus to the pressure applicating band via a pressure supporting plate, the band being assembled to the pressure supporting plate by inserting the band through at least one aperture within the pressure supporting plate.

18. A method of relieving discomfort resulting from menstruation as recited in claim 14, the method further comprising a step of securing a pressure applicating band comprising a band strap and a plurality of stylus, wherein at least one of the plurality of stylus is positioned in registration with the menstrual discomfort controlling pressure point.

19. A method of relieving discomfort resulting from menstruation as recited in claim 18, the method further comprising a step of securing the plurality of stylus in position using a pressure supporting plate, wherein the plurality of stylus are disposed upon the pressure supporting plate, the band being assembled to the pressure supporting plate by inserting the band through at least one aperture through the pressure supporting plate.

* * * * *